United States Patent
Gerndt et al.

(10) Patent No.: US 7,740,786 B2
(45) Date of Patent: Jun. 22, 2010

(54) PROCESS FOR MAKING NECKED NONWOVEN WEBS HAVING IMPROVED CROSS-DIRECTIONAL UNIFORMITY

(75) Inventors: Robert J. Gerndt, Roswell, GA (US); David W. Hall, Alpharetta, GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 1121 days.

(21) Appl. No.: 11/304,144

(22) Filed: Dec. 15, 2005

(65) Prior Publication Data

US 2007/0138698 A1   Jun. 21, 2007

(51) Int. Cl.
B29C 53/24 (2006.01)
B29C 55/02 (2006.01)

(52) U.S. Cl. .............. 264/287; 264/284; 264/286; 264/289.3; 264/289.6; 264/290.2; 264/290.7; 264/288.4; 425/303; 425/336; 425/369

(58) Field of Classification Search .............. 264/284.4, 264/286, 287, 288.2, 289.3, 289.6, 290.2, 264/290.7; 425/303, 336, 369; 162/280
See application file for complete search history.

(56) References Cited

U.S. PATENT DOCUMENTS

| | | | |
|---|---|---|---|
| 654,884 A | 7/1900 | Ferres et al. | |
| 775,495 A | 11/1904 | McConnell | |
| 2,158,087 A | 5/1932 | Rowe et al. | |
| 2,335,313 A * | 11/1943 | Morris et al. | 264/282 |
| 2,481,049 A | 9/1949 | Stamm et al. | |
| 2,494,431 A * | 1/1950 | Eckstein | 425/396 |
| 2,547,736 A * | 4/1951 | Blake | 264/286 |
| 2,710,043 A | 6/1955 | Hubmeier | |
| 2,793,676 A | 5/1957 | Hubmeier | |
| 3,002,876 A | 10/1961 | Rosati | |
| 3,692,618 A | 9/1972 | Dorschner et al. | |
| 3,849,241 A | 11/1974 | Butin et al. | |
| 3,949,127 A | 4/1976 | Ostermeier et al. | |
| 4,016,319 A | 4/1977 | Marshall | |
| 4,100,324 A | 7/1978 | Anderson et al. | |
| 4,289,470 A * | 9/1981 | Johnston et al. | 425/336 |
| 4,295,251 A | 10/1981 | Tatham et al. | |
| 4,340,563 A | 7/1982 | Appel et al. | |
| 4,443,513 A | 4/1984 | Meitner et al. | |
| 4,663,220 A | 5/1987 | Wisneski et al. | |

(Continued)

FOREIGN PATENT DOCUMENTS

CA  758794  5/1967

(Continued)

OTHER PUBLICATIONS

Oxford English Dictionary, Draft Revision, Mar. 2009, "nip".*

Primary Examiner—Christina Johnson
Assistant Examiner—Magali P Théodore
(74) Attorney, Agent, or Firm—Dority & Manning, P.A.

(57) ABSTRACT

Necked nonwoven webs having improved cross-directional uniformity are made by a process which includes the step (prior to neck stretching) of corrugating the nonwoven web to reduce its width from an initial width A to a reduced corrugated width B. The cross-directional uniformity is optimized as the corrugated width B approaches the ultimate width C of the necked nonwoven web.

20 Claims, 9 Drawing Sheets

U.S. PATENT DOCUMENTS

| | | | |
|---|---|---|---|
| 4,720,415 | A | 1/1988 | Vander Wielen et al. |
| 4,741,949 | A | 5/1988 | Morman et al. |
| 4,762,520 | A | 8/1988 | Wallström |
| 4,789,699 | A | 12/1988 | Kieffer et al. |
| 4,965,122 | A * | 10/1990 | Morman .................. 442/328 |
| 4,981,747 | A | 1/1991 | Morman |
| 4,986,105 | A | 1/1991 | Hoglund |
| 5,028,289 | A | 7/1991 | Rasmussen |
| 5,116,662 | A | 5/1992 | Morman |
| 5,156,793 | A | 10/1992 | Buell et al. |
| 5,185,052 | A | 2/1993 | Chappell et al. |
| 5,226,992 | A * | 7/1993 | Morman .................. 156/62.4 |
| 5,336,545 | A | 8/1994 | Morman |
| 5,366,793 | A | 11/1994 | Fitts, Jr. et al. |
| 5,456,971 | A | 10/1995 | Fahmy |
| 5,492,753 | A | 2/1996 | Levy et al. |
| 5,514,470 | A | 5/1996 | Haffner et al. |
| 5,560,793 | A | 10/1996 | Ruscher et al. |
| 5,622,772 | A | 4/1997 | Stokes et al. |
| 5,707,468 | A | 1/1998 | Arnold et al. |
| 5,755,902 | A | 5/1998 | Reynolds |
| 5,789,065 | A | 8/1998 | Haffner et al. |
| 5,807,292 | A | 9/1998 | Delmore |
| 5,883,028 | A | 3/1999 | Morman et al. |
| 6,001,460 | A | 12/1999 | Morman et al. |
| 6,028,240 | A | 2/2000 | Wessel et al. |
| 6,069,097 | A | 5/2000 | Suzuki et al. |
| 6,255,236 | B1 | 7/2001 | Cree et al. |
| 6,803,009 | B2 | 10/2004 | Morman et al. |
| 6,900,147 | B2 | 5/2005 | Morman et al. |

FOREIGN PATENT DOCUMENTS

| | | |
|---|---|---|
| EP | 0 396 800 A1 | 11/1990 |
| EP | 0 602 613 A1 | 6/1994 |
| EP | 0 650 714 | 5/1995 |
| EP | 0 788 874 | 8/1997 |
| EP | 0 810 078 | 12/1997 |
| GB | 2 114 174 A | 8/1983 |
| JP | 09 285488 | 11/1997 |
| WO | WO 92/16371 | 10/1992 |
| WO | WO 99/37841 | 7/1999 |
| WO | WO 00/06377 | 2/2000 |
| WO | WO 00/16974 | 3/2000 |
| WO | WO 00/29199 | 5/2000 |
| WO | WO 01/00915 | 1/2001 |
| WO | WO 01/12427 | 2/2001 |
| WO | WO 01/30563 | 5/2001 |
| WO | WO 2005/065947 | 7/2005 |
| WO | WO 2006/044814 | 4/2006 |
| WO | WO 2006/073975 | 7/2006 |

* cited by examiner

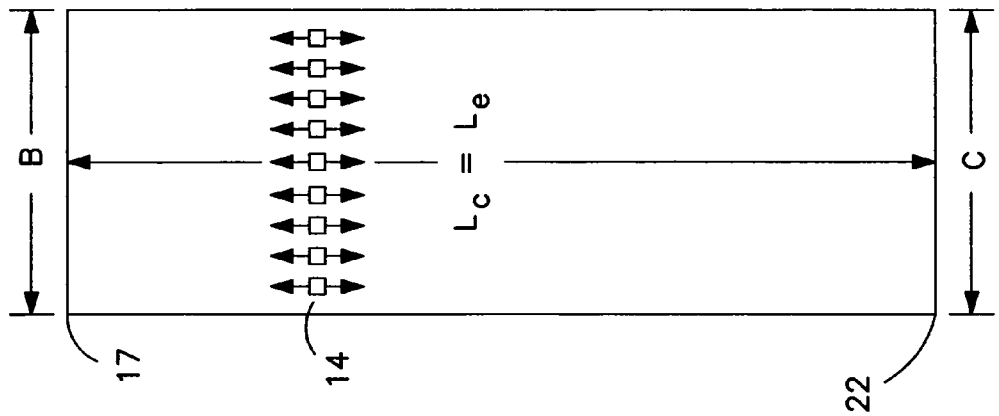
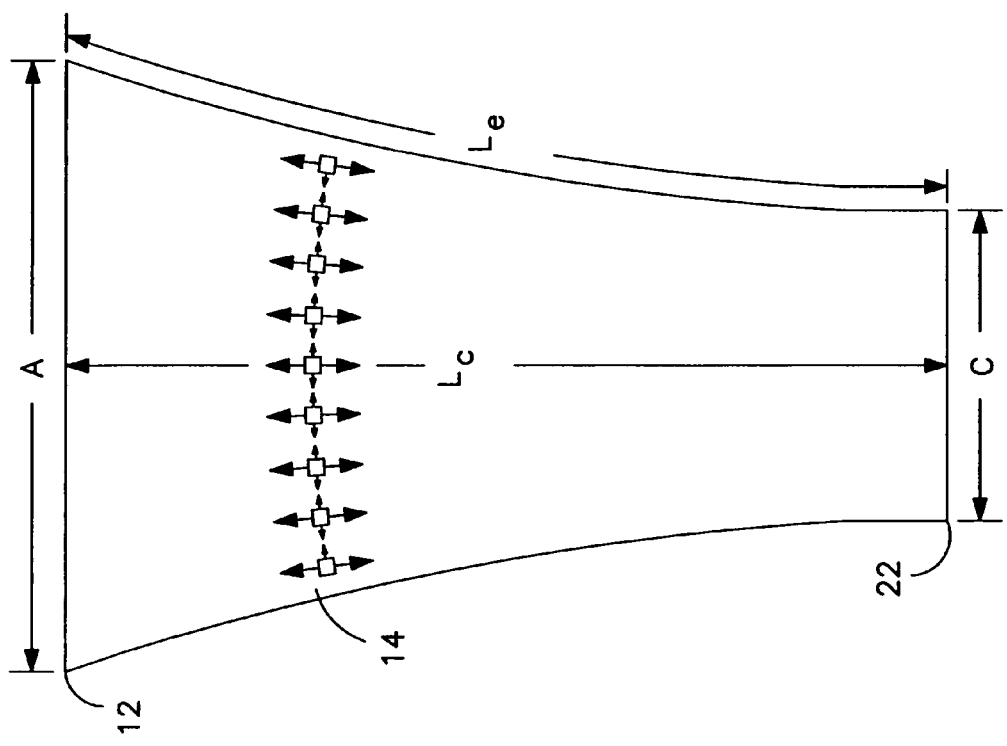

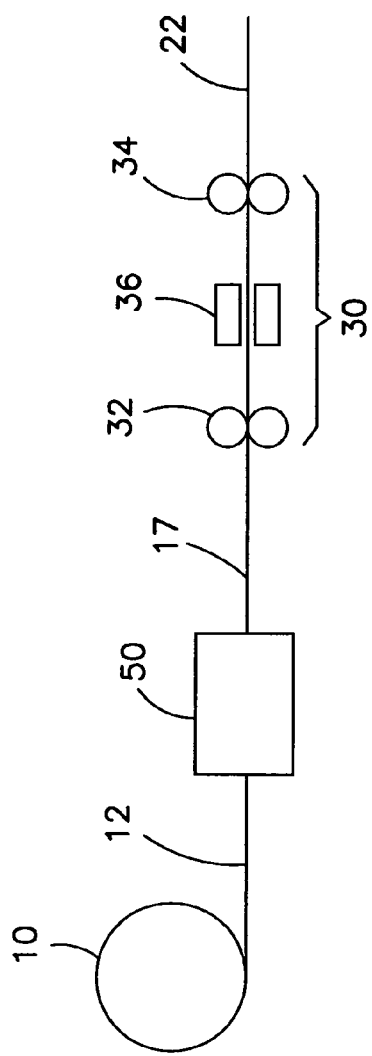
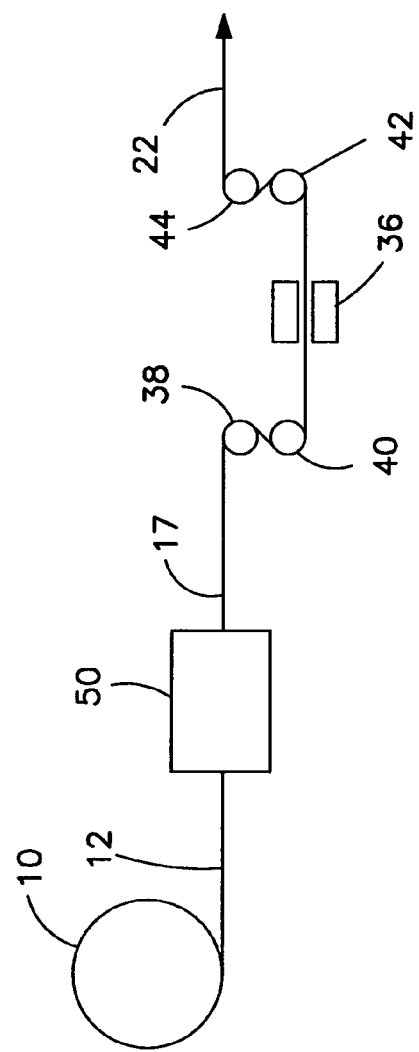

PROCESS FOR MAKING NECKED NONWOVEN WEBS HAVING IMPROVED CROSS-DIRECTIONAL UNIFORMITY

BACKGROUND OF THE INVENTION

This invention is related to a process for making necked nonwoven webs and laminates having more uniform basis weights and stretching properties in the cross direction.

Necked nonwoven webs, including necked spunbond webs, meltblown webs, combinations and the like, are often made using a process which is schematically illustrated in FIG. 1. A nonwoven, web 12 having a starting width A is passed in its machine direction between a first nip 16, which can be a first pair of nip rollers traveling at a first surface velocity, and a second nip 26, which can be a second pair of nip rollers traveling at a second surface velocity which is faster than the first surface velocity. The surface velocity difference between the first and second nips results in formation of a narrower ("necked") nonwoven web 22 having a necked width C which is less than the starting width A.

The necked nonwoven web 22 generally includes fibers which are closer together and more aligned in the machine direction than the fibers of the starting nonwoven web 12, which can be more randomly aligned. The necking may be performed with the aid of heat applied below the melting temperature of the fibers, for instance, by placing an oven or other heat source between the first and second nips. The necked nonwoven web 22 may also be heat set, either during or after the necking process, so that the necked web becomes somewhat stable. A nonwoven web which is stable in the necked condition is said to be "reversibly necked". A reversibly necked nonwoven web can be easily extended in the cross direction by applying a small extension force, and tends to return to its narrower, necked configuration when the extension force is released.

The starting nonwoven web 12 includes edge regions 13 and 15, and a central region 11. The necked nonwoven web 22 includes edge regions 23 and 25, and a central region 21. Because the necking causes the nonwoven fibers to become closer together and more aligned, without noticeably stretching or narrowing the individual fibers, the necked nonwoven web 22 generally has a higher basis weight than the starting nonwoven web 12.

As can be easily seen from FIG. 1, the nonwoven fibers in the edge regions 13 and 15 of the starting nonwoven web travel a greater distance between the first nip 16 and the second nip 26 of the necking process, than the fibers in the central region 11. This results in more extension of the web at the edges and increased fiber gathering and necking in the edge regions.

A second and independent cause of greater necking at the web edges results from the curvature of the web edges under tension. From biaxial stress analysis as shown in FIG. 2C, it can be shown that the web tension in the curved edge regions 13 and 15 creates a cross-directional stress field which is greater at the center region than at the edges. This cross-directional stress field counteracts the compressive forces which cause necking of the web, counteracting more forces at the center region 11 and less forces at the edge regions 13 and 15.

Consequently, the fibers in the edge regions 23 and 25 of the necked nonwoven web are generally more aligned and closer together than the fibers in the central region 21. As a result, the necked nonwoven web may be nonuniform in the cross direction, having a higher basis weight in both edge regions than in the central region, and having greater cross-directional extendibility in both edge regions than the central region.

Various techniques for producing necked nonwoven webs having improved cross-directional uniformity are described in U.S. Pat. Nos. 6,803,009 and 6,900,147, both issued to Morman et al. The disclosed techniques involve modifications to the necking process and/or material being necked. There is a need or desire for a necking process which achieves cross-directional uniformity in a self-regulating and self-controlling fashion without requiring modification of existing necking equipment or compositional modifications to the material being necked.

SUMMARY OF THE INVENTION

The present invention is directed to a process for making a necked nonwoven web having improved cross-directional uniformity. The process includes the steps of providing a nonwoven web having an initial (first) width A in the cross-direction and reducing the width of the nonwoven web to a second width B without stretching the nonwoven web in the machine direction (i.e., prior to neck stretching the nonwoven web). This reduction in width is suitably accomplished by corrugating the nonwoven web in the cross direction.

Then, the corrugated nonwoven web is neck stretched in the machine direction to produce a necked nonwoven web having a third width C which is less than the first width A. The neck stretching is suitably accomplished by passing the corrugated nonwoven web through a first nip having a first surface velocity, and a second nip having a second surface velocity which is higher than the first surface velocity. The neck stretching reduces the corrugations but may not significantly change the width of the nonwoven web. The second width B is suitably closer to the third width C than to the first width A, and may be about the same as the third width C.

By reducing the width of the nonwoven web prior to neck stretching, and by minimizing the change in width during neck stretching, the nonuniformities that would result from a width reduction during neck stretching are also minimized. The resulting necked nonwoven web has a substantially uniform basis weight resulting from uniform neck stretching across its width. The substantial uniformity of the necked nonwoven web results in less waste material and higher quality end products.

BRIEF DESCRIPTION OF THE DRAWINGS

FIGS. 2A and 2B schematically illustrate how reducing the width of a nonwoven web prior to neck stretching may substantially eliminate any differences in tension and stretching that would otherwise be experienced across the width of the nonwoven web.

FIGS. 3A and 3B schematically illustrate processes for making a necked nonwoven web according to the invention.

DEFINITIONS

Figure 1:
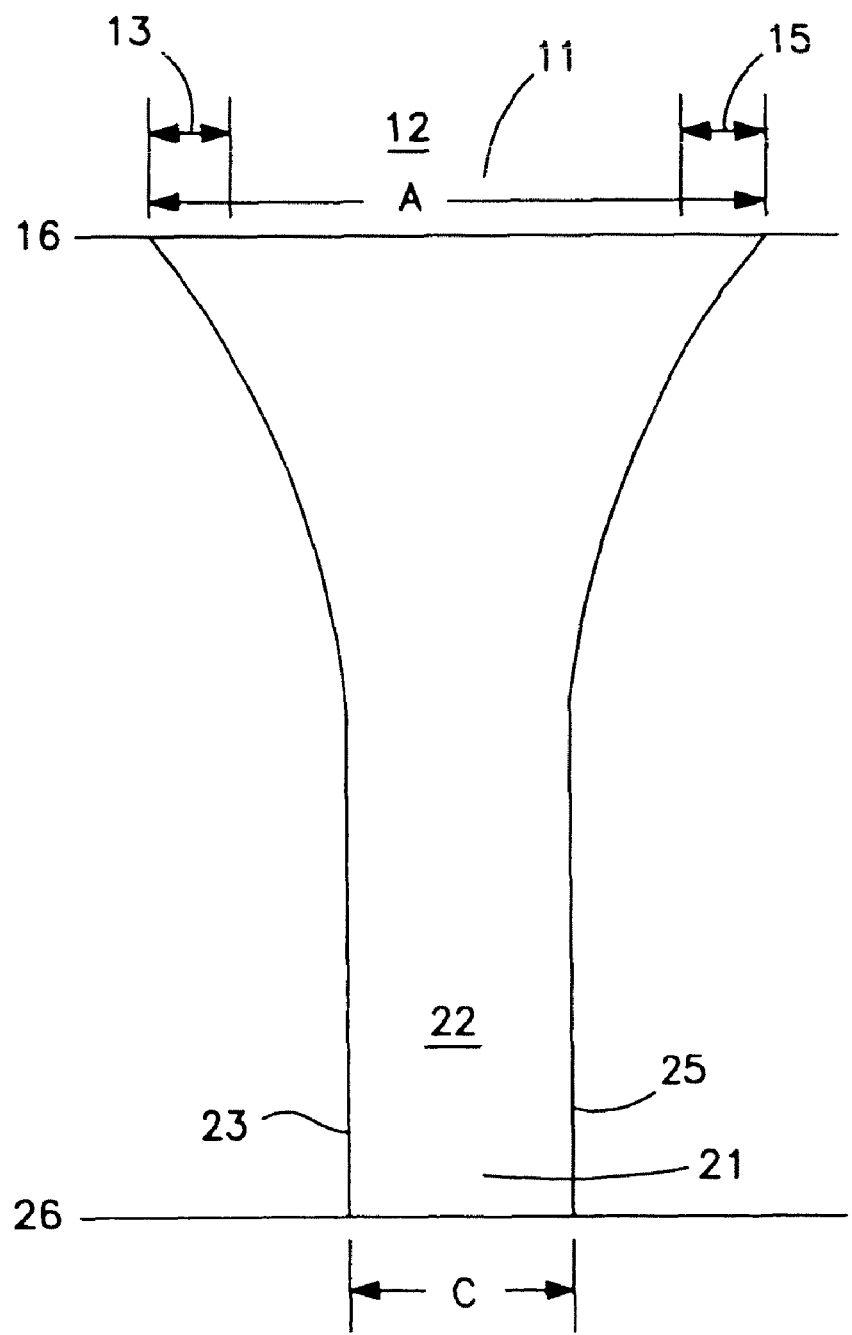
FIG. 1 schematically illustrates a conventional necking process as described in the foregoing "Background Of The Invention."

The term "corrugations" includes pleats, waves, folds, wrinkles, ruffles and any other Z-directional distortions that can be imparted to a nonwoven web to reduce its width in the cross direction without increasing its length in the machine direction. The term "corrugating" refers to any process for forming corrugations in the nonwoven web.

The term "cross direction" refers to the width direction laterally perpendicular to the primary direction of travel of the nonwoven web in a process, and is typically perpendicular to the primary direction of manufacture of the nonwoven web and its fibers. The term "machine direction" refers to the length direction parallel to the primary direction of travel of the nonwoven web in a process.

The term "necked material" refers to any material which has been consolidated in one direction (e.g., a width direction) by stretching in a perpendicular direction (e.g., a machine direction).

The term "neckable material" means any material which can be necked.

The term "nonwoven web" means a web that has a structure of individual fibers of threads which are interlaid, but not in an identifiable repeating manner. Nonwoven webs have been, in the past, formed by a variety of processes such as, for example, spunbond processes, meltblowing processes and bonded carded web processes.

The term "spunbonded fibers" refers to small diameter fibers which are formed by extruding a molten thermoplastic material as filaments from a plurality of fine, usually circular, capillaries in a spinnerette with the diameter of the extruded filaments then being rapidly reduced, for example, by eductive drawing or other well-known spun bonding mechanisms. The production of spun-bonded nonwoven webs is illustrated in patents such as, for example, in U.S. Pat. No. 4,340,563 to Appel et al., and U.S. Pat. No. 3,692,618 to Dorschner et al. The disclosures of both these patents are hereby incorporated by reference.

The term "meltblown fibers" means fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameters, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, the disclosure of which is hereby incorporated by reference.

The term "microfibers" means small diameter fibers having an average diameter not greater than about 100 microns, for example, having a diameter of from about 0.5 microns, more specifically microfibers may also have an average diameter of from about 4 microns to about 40 microns.

The term "interfiber bonding" means bonding produced by thermal bonding or entanglement between the individual nonwoven fibers to form a coherent web structure. Fiber entangling is inherent in the meltblown processes but may be generated or increased by processes such as, for example, hydraulic entangling or needle punching. One or more thermal bonding steps are employed in most processes for forming spunbond webs. Alternatively and/or additionally, a bonding agent can be utilized to increase the desired bonding and to maintain structural coherency of the web. For example, powdered bonding agents and chemical solvent bonding may be used.

The "central region" of a nonwoven web is defined as the central 70% of the cross-directional width of the nonwoven web. The "edge regions" are defined as the outermost 15% of the width on both sides of the central region of the nonwoven web.

The term "elastic" refers to a material which can be stretched by about 50% of its original dimension in at least one direction and will, upon removal of the stretching force, recover at least 50% of the stretching. For example, an elastic material having a dimension of 100 cm may be stretched to a dimension of at least 150 cm without rupturing, and will recover to a dimension of 125 cm or less when the stretching force is removed. Many elastic materials may stretch by at least 75%, or at least 100%, or at least 200% of an original dimension without rupture, and may recover at least 60%, or at least 80%, or substantially all of the stretching when the stretching force is removed.

The term "extendible" refers to materials which exhibit the stretch properties of elastic materials but not the recovery properties (i.e., materials which can be stretched by at least 50% and recover zero to less than 50% of the stretching).

The term "reversibly necked material" refers to a necked material that has been treated while necked to impart memory to the material so that, when a force is applied to extend the material to its pre-necked dimensions, the necked and treated portions will generally recover to their necked dimensions upon termination of the force. One form of treatment is the application of heat. Generally speaking, extension of the reversibly necked material is substantially limited to extension to its pre-necked dimensions. Therefore, unless the material is elastic, extension too far beyond its pre-necked dimensions will result in material failure. A reversibly necked material may include more than one layer, for example, multiple layers of spunbonded web, multiple layers of meltblown web, multiple layers of bonded carded web or any other suitable combination or mixtures thereof, as described in U.S. Pat. No. 4,965,122, which is incorporated by reference.

DETAILED DESCRIPTION OF THE INVENTION

Referring to FIGS. 3A and 3B, a process for making a necked nonwoven material 22 includes the step of providing a nonwoven web 12 in an un-necked state, such as by unwinding it from a storage roll 10. The nonwoven web 12, which has a first width A, is passed through a corrugating station 50 (described further below). The station 50 corrugates the nonwoven web, and provides a corrugated nonwoven web 17 having a reduced width B which is less than the width A.

The desired reduced width B is best described with respect to the necked width C, which is the ultimate desired width of the necked nonwoven web. Referring to FIG. 2A, the prior art processes necked the nonwoven web from a starting width A, to provide a necked nonwoven web 22 having a necked width C. The necking was performed by stretching the nonwoven web in the machine direction to cause narrowing in the cross direction. The machine direction stretching in the center of the nonwoven web proceeded along a path $L_c$, whereas stretching along the edges of the nonwoven web proceeded along a visibly longer path $L_e$. The longer stretching path $L_e$ resulted in greater tension, greater consolidation of fibers and a greater increase in basis weight along the edges of the nonwoven web, compared to the center. A second source of non-uniform necking is the non-uniform cross-direction stress field (previously explained) that is set up by the tension in the curved edges. These two effects are additive in causing the necked nonwoven web to be significantly non-uniform in basis weight and other important properties.

Figure 2C:
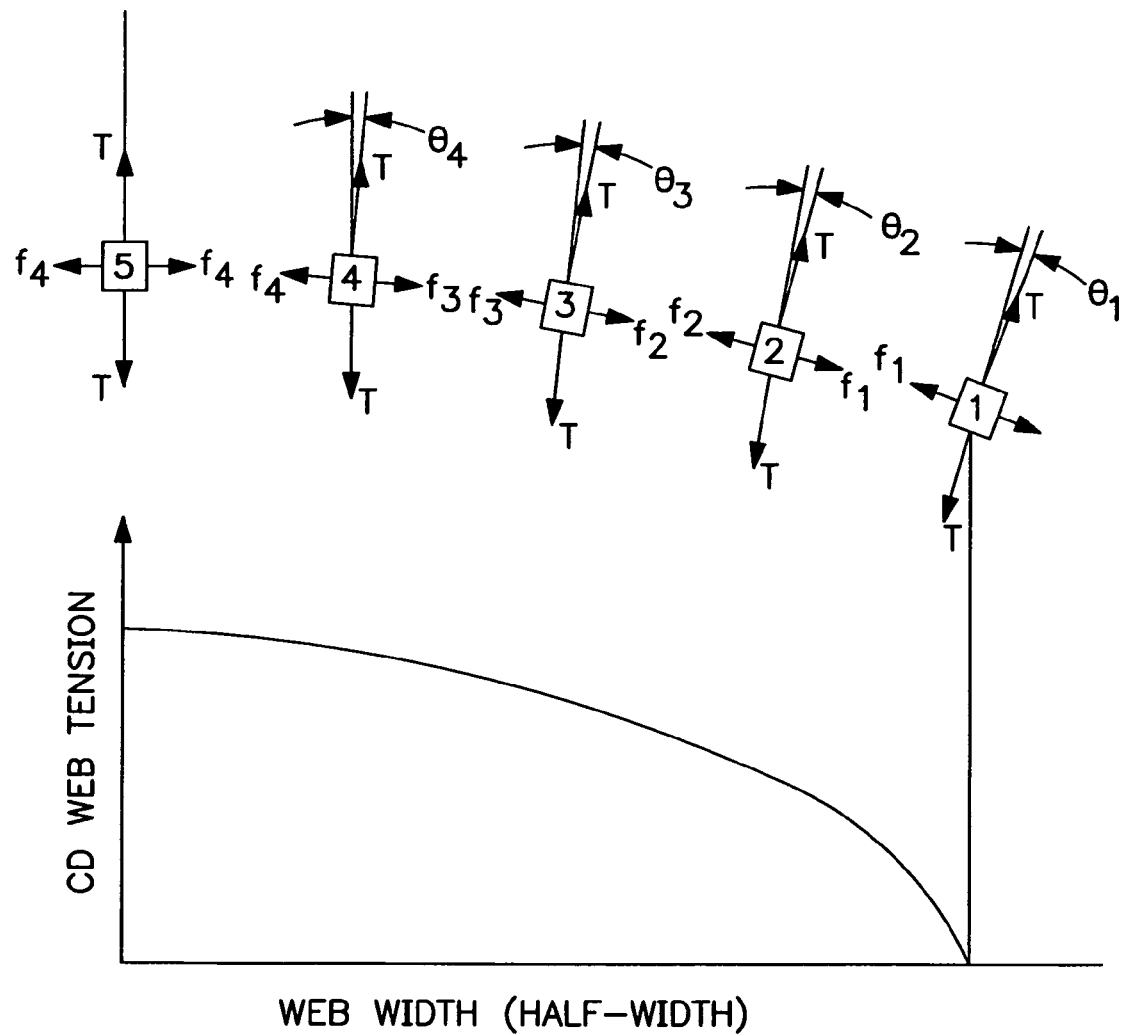
FIG. 2C graphically illustrates a biaxial stress field existing across one-half of the width of the nonwoven web illustrated in FIG. 2A.

Referring to FIG. 2A, the biaxial stress field 14 is represented by a series of small vector (force) diagrams existing across the width of the nonwoven web 12 during neck stretching. FIG. 2C graphically illustrates an enlarged view of the forces across one-half of the same nonwoven web 12 at evenly spaced locations 1, 2, 3, 4 and 5. It is readily apparent that the forces are non-uniform across the cross-directional width of nonwoven web 12.

Referring to FIG. 2C, the lateral (cross-directional) forces at box locations 1, 2, 3, 4 and 5 are represented as $f_1$, $f_2$, $f_3$, and $f_4$. The longitudinal (machine-directional) forces at each location are represented as "T." The angles $\theta_1$, $\theta_2$, $\theta_3$, $\theta_4$ and $\theta_5$ represent the angular differences between the direction of tension "T" existing at the top of each box (1, 2, 3, 4 and 5) opposite the direction of neck stretching, and the opposing direction of tension "T" at the bottom of each box (1, 2, 3, 4 and 5) in the direction of neck stretching. The forces "f" are related according to the following equations.

$$f_1 = 2TS\ln\frac{\theta_1}{2}$$
$$f_2 = f_1 + 2TS\ln\frac{\theta_2}{2}$$
$$f_3 = f_2 + 2TS\ln\frac{\theta_3}{2}$$
$$f_4 = f_3 + 2TS\ln\frac{\theta_4}{2}$$
$$\theta_1 > \theta_2 > \theta_3 > \theta_4 \ \theta_5 = 0°$$

In summary, the cross-directional force during neck stretching increases toward the edges of the nonwoven web 12 and approaches zero at the center.

FIG. 2B illustrates the desired relationship between the reduced width B of the corrugated nonwoven web 17, and the necked width C of the necked nonwoven web 22. As shown in FIG. 2B, if the corrugated nonwoven web enters the necking process with a reduced width B that is identical to the necked width C, then the stretching length of path $L_c$ at the center of the nonwoven web is identical to the stretching length of path $L_e$ at both lateral edges and the tension along the edges is aligned with the web travel (machine) direction, eliminating the biaxial stress field. The differences in tension, consolidation of fibers and basis weight increase between the center and edges of the nonwoven web, resulting from the necking process, are substantially eliminated when the corrugated width B is equal to the desired necked width C. The stress field 14 is essentially uniaxial, and cross-directional forces are minimized or eliminated.

It should be apparent from FIGS. 2A and 2B that any reduction of the second (corrugated) width B compared to the first (starting) width A would result in a necked nonwoven web 22 having improved cross-directional uniformity. For significantly improved results, the second width B should be closer to the third (necked) width C than to the first width A. Suitably, the second width B may be within about 15% of the third width C, or about the same as the third width C.

Moreover, in order to realize the benefits of neck stretching, the third width C should be at least 25%, or at least 50% or at least 75% less than the first width A. Accordingly, the second width B is advantageously at least 25%, or at least 50%, or at least 75% less than the first width A.

Referring again to FIGS. 3A and 3B, the corrugated nonwoven web 17 is then passed through a conventional necking station 30 to form the necked nonwoven web 22 having the necked width C. In the embodiment of FIG. 3A, the necking station 30 includes a first pair of counterrotating nip rollers 32 having a first surface velocity, a second pair of counterrotating nip rollers 34 having a second surface velocity higher than the first, and an optional heating device or oven 36 to aid in the necking process between the first and second pairs of nip rollers. The second pair of nip rollers 36 may suitably have a second surface velocity which is at least about 1.05 times, or about 1.1-1.7 times, or about 1.2-1.5 times the first surface velocity of the first pair of nip rollers 32. The optional heating device 36 may facilitate a neck stretching temperature ranging from ambient temperature (about 25° C.) to a temperature which is at least 10° C. below the softening temperature of the polymer in the nonwoven web.

In the embodiment of FIG. 3B, the necking station includes four co-rotating rollers 38, 40, 42 and 44 arranged in two S-wrap relationships relative to the nonwoven web. The oven 36 is located between rollers 40 and 42 The rollers 38, 40, 42 and 44 may have progressively faster surface velocities, so that the corrugated nonwoven web 17 is neck stretched to a length that is at least about 1.05 times, or about 1.1-1.7 times, or about 1.2-1.5 times its original length in the machine direction. One or more of the rollers may optionally be heated to facilitate the neck stretching.

Figure 4A:
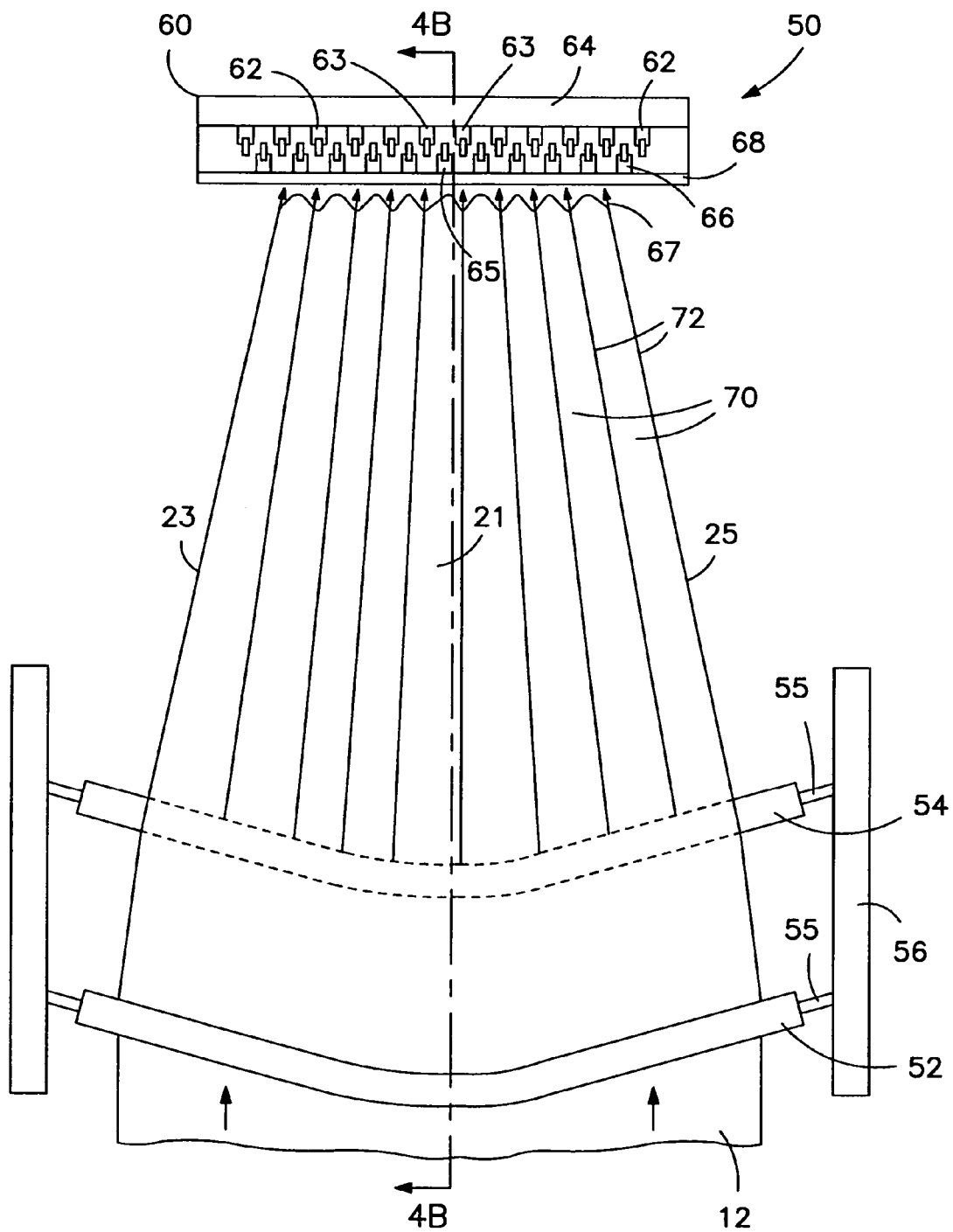
FIGS. 4A to 4E schematically illustrate apparatus for corrugating the nonwoven webs prior to necking.
Figure 4B:
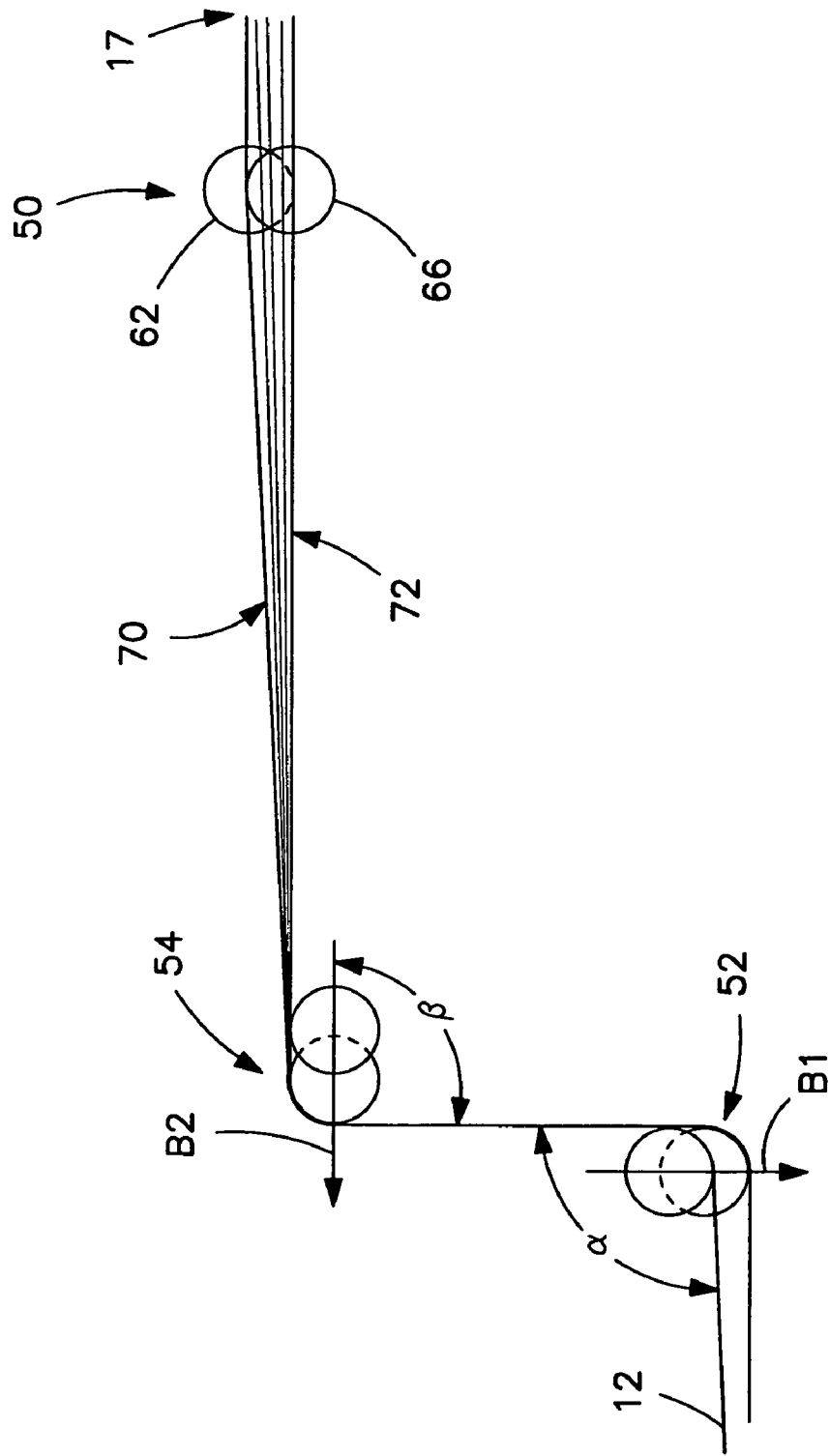

FIG. 4A illustrates one embodiment of a corrugating station 50 useful for forming the corrugated nonwoven web 50 prior to necking. FIG. 4B is a sectional view taken along line 4B-4B in FIG. 4A. The corrugating station 50 is designed to reduce the width of the nonwoven web in the cross direction, by forming corrugations, without increasing its length in the machine direction. If there is an incidental increase in length resulting from the corrugating station, it should not exceed 5% of the starting length of the nonwoven web. During the subsequent neck stretching, the length of the nonwoven web is significantly increased and the corrugations are reduced in size, or substantially eliminated.

In the corrugating station 50 of FIG. 4A, the nonwoven web 12 having a first width A is fed underneath a first bowed roller or bar 52, then over a second, subsequent bowed roller or bar 54, both of which are mounted to a frame 56. The purpose of the bowed rollers is to aim or direct the nonwoven web 12 along a narrowing path, so that various parts of the nonwoven web, including its edge regions, are directed toward its center.

For purposes of illustration, the amount of bowing of the rollers or bars 52 and 54 is somewhat exaggerated in FIG. 4A. Typically, the first bowed roller or bar 52 should have a first bow amount which is about 5-10% of its width. The second bowed roller or bar 54 should have a second bow amount which is about 10-15% of its width. The relationship between the desired first bow amount and the second bow amount is roughly proportional to the relationship between the desired second (corrugated) width B and the first (initial) width A of the nonwoven web. For instance, if the desired corrugated width B is 50% of the initial width A, then the first bow amount (percentage) of the first roller or bar 52 should be about 50% of the second bow amount (percentage) of the second roller or bar 54.

As shown in FIG. 4B, the bowed roller or bar 52 is suitably bowed in a direction indicated by arrow B1. The bowed roller or bar 54 is suitably bowed in a mutually perpendicular direction indicated by arrow B2. The bowed rollers or bars 52 and 54 are suitably positioned so that the nonwoven web 12 changes direction by angles "alpha" and "beta", each being about 90 degrees, as the nonwoven web passes each bowed roller or bar.

In order to permit rotation, bowed rollers 52 and 54 may be formed of a resilient (i.e., flexible) material, such as various types of rubber, and may be mounted to rigid rotatable end shafts 55. The rollers 52 and 54 may be separately powered or driven by the movement of nonwoven web 12. Alternatively, bowed bars may be used instead of bowed rollers. Bowed bars would not rotate, but would have smooth surfaces so the nonwoven web 12 can easily slide across them.

After passing between the bowed rollers or bars, the nonwoven web 12 is directed toward a castor roll assembly 60 which includes an upper row of castor rollers 62 mounted to an upper frame 64 and a lower row of castor rollers 66 mounted to a lower frame 68. Most of the castor rollers 62 and 66 are swivel-mounted and can pivot to the left or right. However, one or more castor rollers 63 and 65 in the center of each row may be rigidly mounted to avoid pivoting. Alternatively, all of the castor rollers can be rigidly mounted in directions aligned with the diverging web at each location across the nonwoven web 12.

The nonwoven web 12 is pulled between the upper row 62 and the lower row 66 of castor rollers in the direction of the small arrows 67. Because the upper and lower rows 62 and 66 of castor rollers are offset from each other, the nonwoven web is bent and folded by the castor rollers into a corrugated configuration including corrugations defined by a plurality of alternating peaks 70 and valleys 72. Because the nonwoven web is under slight tension as it is being pulled, the peaks 70 and valleys 72 begin to form immediately after the nonwoven web leaves the second bowed roller or bar 54. The nonwoven web 12 narrows, and the peaks and valleys 70 and 72 become more pronounced, as the nonwoven web 12 enters the castor roll assembly 60. The peaks and valleys 70 and 72 reach maximum height as the nonwoven web passes between the upper and lower rows 62 and 66 of castor rollers. The corrugated nonwoven web 17 then exits the castor roll assembly 60 and the corrugating station 50, and proceeds toward the necking station 30 (FIGS. 3A and 3B).

In the case where the castor rollers 62 and 66 are swivel-mounted, they may pivot as needed to reflect the angles in the corrugations caused by the narrowing of the nonwoven web. It is advantageous to have one or more centrally located castor rollers 63 and 65 rigidly mounted to prevent pivoting, because the nonwoven web experiences its highest tension in the corrugating station 50 at the central location 21.

While it is possible to vary the lateral distance between castor rollers in the upper and lower rows 62 and 66, the primary purpose of the castor roller assembly 60 is to provide a nonwoven web of reduced width B which is corrugated as uniformly as possible. To this end, the castor rollers in the upper row 62 are suitably uniformly spaced from each other. The castor rollers in the lower row 66 are suitably uniformly spaced from each other and positioned halfway in between the nearest castor rollers in the upper row 62.

Figure 4C:
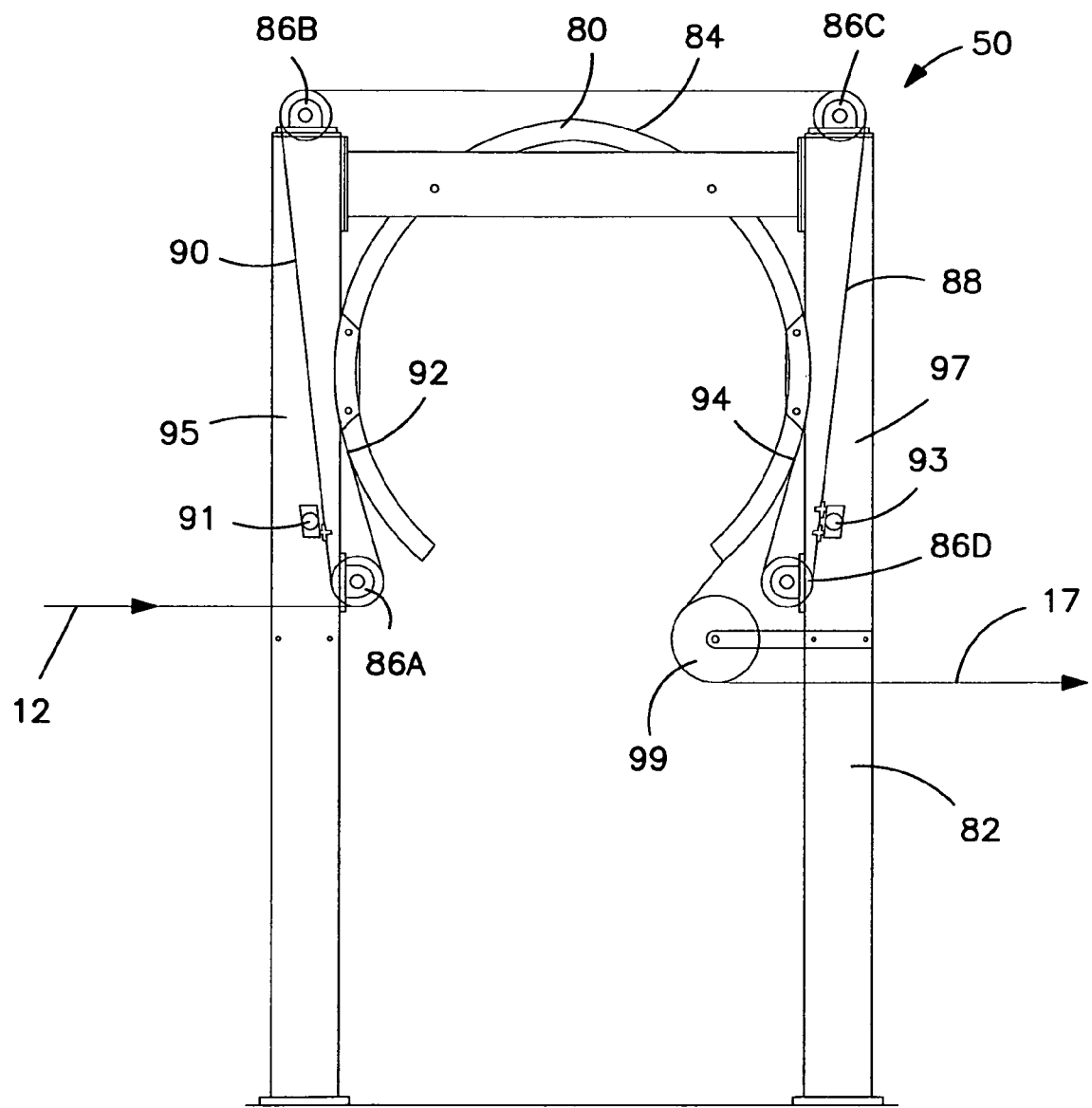
Figure 4D:
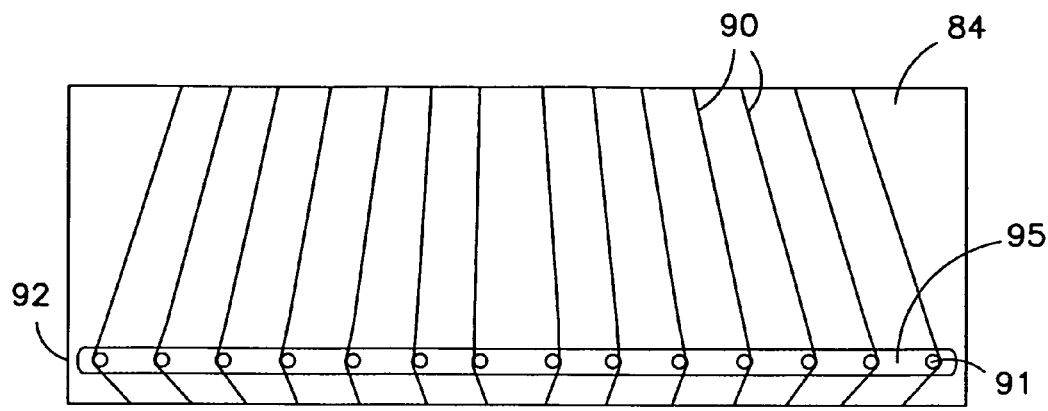
Figure 4E:
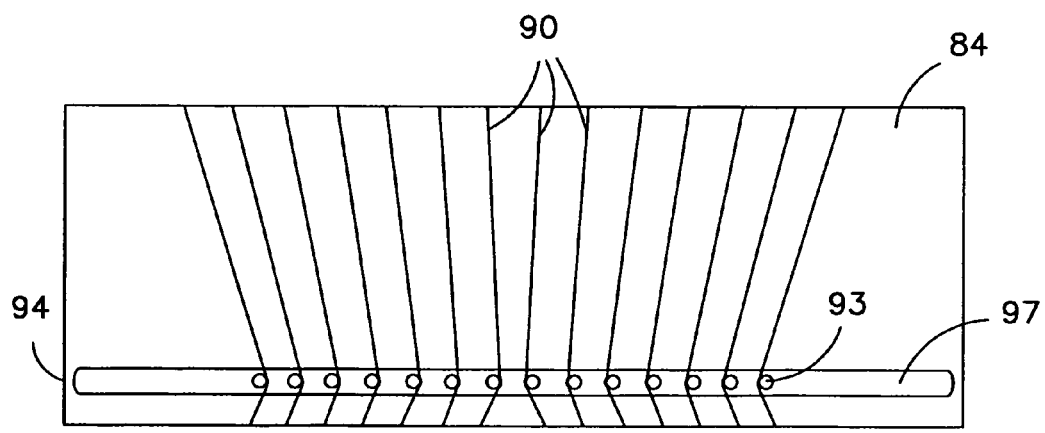

FIGS. 4C through 4E illustrate a second embodiment of a corrugating station 50 which utilizes moving cords 90 that become progressively closer while carrying the nonwoven web across a non-rotating cylindrical surface. FIG. 4C is a side view of this process, and illustrates a cylinder 80 mounted to a frame 82 and having an outer surface 84. The nonwoven 12 is conveyed to the cylindrical surface 84 in the direction of the arrow, and is pulled around the cylindrical surface with the aid of a drive roll 86D whereupon it exits the cylindrical surface 84 as a corrugated nonwoven web 17 after turning on ider roll 99. Cords 90 suitably have some resilience, and can be made of one piece of material and arranged as an endless cord which crosses over from the back to the front of the cylinder 80 in order to repeat the traversing of the circuits from front to back.

FIG. 4D illustrates a front view of cylinder 80 as viewed from the left of the corrugating station 50 shown in FIG. 4C. FIG. 4E illustrates a back view of cylinder 80 as viewed from the right of the corrugating station 50. As shown, the cylinder 80 is equipped with a plurality of continuously moving, non-intersecting cords 90 which become progressively closer together between the location 92 where the nonwoven web 12 first contacts the cylindrical surface 84 and the location 94 where the cords 90 leave the cylinder 80. The cords 90 are guided by small guide pins or pulleys 91 and 93 mounted to frames 95 and 97 above the cylindrical surface 84. The guide pins or pulleys are suitably rotatable.

Referring again to FIG. 4C, the cords 90 approach the cylinder 80 at location 92, leave the cylinder 80 at location 94, and are driven around the cylinder 80 by an arrangement of four pulleys 86A, 86B, 86C and 86D. The nonwoven web 12, which is also guided by pulley 86A, approaches the cylindrical surface 84 and is sandwiched between the cords 90 and the cylindrical surface 84. As the nonwoven web is transported around the cylindrical surface 84, the moving cords 90 become progressively closer to each other, causing the nonwoven web to gather between the cords 90 and become corrugated. The ratio of the distance between cords 90 at exit location 94 and entrance location 92 is proportional to the ratio of the corrugated width B to the initial width A of the nonwoven web. If the desired corrugated width B is 50% of the initial width A, then the distance between adjacent cords 90 at location 94 should be 50% of the distance between them at location 92, as shown in FIGS. 4D and 4E. The cords 90 may be formed of any suitably strong elastomeric materials such as polyurethane, polyethylene, polytetrafluoroethylene or polypropylene.

It should be noted that the corrugating station 50 is not limited to the apparatus described above. Any suitable corrugating apparatus may be employed.

The nonwoven web 12 may be any nonwoven material such as, for example, a spunbond web, meltblown web, bonded carded web or other fibrous web or film. If the nonwoven web 12 is a web of meltblown fibers, it may include meltblown microfibers. The nonwoven web 12 is made from any material that can be treated while necked so that, after treatment, upon application of a force to extend the necked material to its pre-necked dimensions, the material recovers generally to its necked dimensions upon termination of the force. A method of treatment is the application of heat. Certain polymers such as, for example, polyolefins, polyesters, polyamides and polycarbonates may be heat treated under suitable conditions to impart such memory.

Polymers suitable for making the nonwoven web 12 include those polymers known to be generally suitable for making nonwoven webs such as spunbond, meltblown, carded webs and the like, and such polymers include for example polyolefins, polyesters, polyamides, polycarbonates and copolymers and blends thereof. It should be noted that the polymer or polymers may desirably contain other additives such as processing aids or treatment compositions to impart desired properties to the fibers, residual amounts of solvents, pigments or colorants and the like.

Suitable polyolefins include polyethylene, e.g., high density polyethylene, medium density polyethylene, low density polyethylene and linear low density polyethylene; polypropylene, e.g., isotactic polypropylene, syndiotactic polypropylene, blends of isotactic polypropylene and atactic polypropylene; polybutylene, e.g., poly(1-butene) and poly (2-butene); polypentene, e.g., poly(1-pentene) and poly(2-pentene); poly(3-methyl-1-pentene); poly(4-methyl-1-pentene); and copolymers and blends thereof. Suitable copolymers include random and block copolymers prepared from two or more different unsaturated olefin monomers, such as ethylene/propylene and ethylene/butylene copolymers. Suitable polyamides include nylon 6, nylon 6/6, nylon 4/6, nylon 11, nylon 12, nylon 6/10, nylon 6/12, nylon 12/12, copolymers of caprolactam and alkylene oxide diamine, and the like, as well as blends and copolymers thereof. Suitable polyesters include poly(lactide) and poly(lactic acid) polymers as well as polyethylene terephthalate, polybutylene terephthalate, polytetramethylene terephthalate, polycyclohexylene-1,4-dimethylene terephthalate, and isophthalate copolymers thereof, as well as blends thereof.

In one embodiment of the present invention, the nonwoven web 12 is a multilayer material having, for example, at least one layer of spunbonded web joined to at least one layer of meltblown web, bonded carded web or other suitable material. For example, the nonwoven web 12 may be a multilayer material having a first layer of spunbonded polypropylene having a basis weight from about 0.2 to about 8 ounces per square yard (osy), a layer of meltblown polypropylene having a basis weight from about 0.1 to about 4 osy, and a second layer of spunbonded polypropylene having a basis weight of about 0.2 to about 8 osy.

Alternatively, the nonwoven web 12 may be single layer of material such as, for example, a spunbonded web having a basis weight of from about 0.2 to about 10 osy or a meltblown web having a basis weight of from about 0.2 to about 8 osy.

The nonwoven web 12 may also be a composite material made of a mixture of two or more different fibers or a mixture of fibers and particulates. Such mixtures may be formed by adding fibers and/or particulates to a gas stream in which meltblown fibers are carried so that an intimate entangled comingling of meltblown fibers and other materials, e.g., wood pulp, staple fibers or particulates such as, for example, superabsorbent materials occurs prior to collection of the fibers upon a collecting device to form a coherent web of randomly dispersed meltblown fibers and other materials such as disclosed in U.S. Pat. No. 4,100,324, the disclosure of which is hereby incorporated by reference.

If the nonwoven web 12 is a nonwoven web of fibers, the fibers should be joined by interfiber bonding using one or more of the bonding processes described in the foregoing "DEFINITION" of interfiber bonding.

The relation between the original width of the nonwoven web 12 to its width after tensioning determines the stretch limits of the necked material 22. For example, if it is desired to prepare a reversibly necked material 22 that can be stretched to a 150 percent elongation (i.e., 250 percent of its necked width) and can recover to within about 25 percent of its neckable width, a nonwoven web 12 having a width A such as, for example, 250 cm, can be corrugated to a reduced width B of about 100 cm, then neck stretched to an equivalent width C of about 100 cm for a percent neck of about 60 percent. While tensioned, it is heat treated to maintain its reversibly necked configuration 22. The resulting reversibly necked material has a width C of about 100 cm and is stretchable to at least the original 250 cm dimension A of the nonwoven web 12 for an elongation or percent stretch of about 150 percent. The reversibly necked material 22 may return to within about 25 percent of its necked width C of about 100 cm, (i.e., to a width of about 125 cm) after release of the stretching force for a recovery of about 83 percent.

Figure 5:
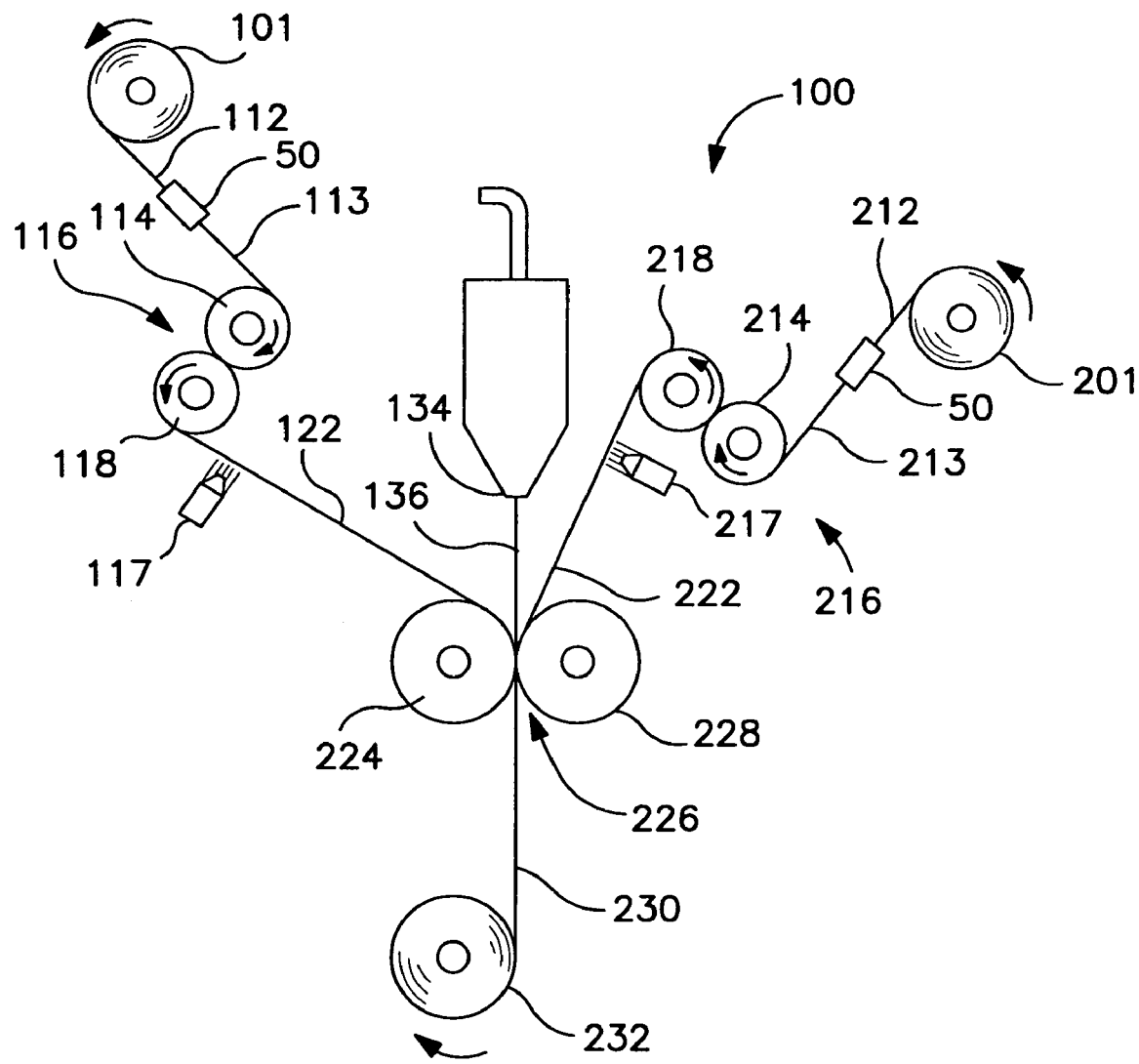
FIG. 5 schematically illustrates a process for forming neck-bonded laminates.

FIG. 5 schematically illustrates a process 100 for preparing a neck-bonded laminate of the invention, including two necked spunbonded webs and an elastomeric film between them. In this process, the elastomeric film is extruded between the two necked spunbond webs. The spunbond webs are heated to enhance the necking.

Referring to FIG. 5, first and second spunbond webs 112 and 212 are unwound from supply rolls 101 and 201 and passed through corrugating stations 50 to form corrugated webs 113 and 213. First corrugated web 113 passes through a first nip 116, including nip rollers 114 and 118, turning at a first surface velocity; and through a second nip 226, including nip rollers 224 and 228, turning at a second surface velocity which is higher than the first surface velocity. Neck stretching of the corrugated web 113 between the first nip 116 and second nip 226 is effected by the different surface velocities, and with the aid of heating device 117. The heating device 117 heats the nonwoven web to a temperature about 10-60° C., suitably about 20-50° C. below the melting temperature of the spunbond fibers.

Second corrugated web 213 passes through a third nip 216 which includes nip rollers 214 and 218, turning at a third surface velocity; and through the above-described second nip 226, including nip rollers 224 and 228, turning at the second surface velocity. The second surface velocity is higher than the third surface velocity, thereby effecting necking between the nips 216 and 226. As illustrated, a heating device 217 is used to heat the nonwoven web.

To make the neck bonded laminate 230, a molten elastomer or other polymer is extruded through a die tip 134 to form an elastomeric or extendible film 136. The film 136 is deposited directly between the tensioned necked spunbond webs 122 and 222, and all three layers are brought together in the nip 226. The film 136 may contact the necked materials 122 and 222 within about 0.1-1.0 second after the film leaves the die tip 134, suitably within about 0.25-0.5 seconds, desirably within about 0.3-0.45 seconds.

The film 136 may be extruded at a temperature of from about 180-300° C., suitably of about 200-250° C.

Sufficient pressure is applied in the nip 226 to thermally bond the elastomeric or extendible film 136 (in a relatively untensioned state) to the tensioned necked, nonwoven webs 122 and 222. The nip rollers 224 and 228 may or may not be patterned, need not be heated, and may be chilled (e.g., to a temperature of about 10-30° C.) so as to quench the film 136 between the necked spunbond webs. The resulting neck-bonded laminate 230 can be stretched in the cross direction due to the extendibility of the necked nonwoven webs. Upon relaxation, the laminate 230 will return substantially to its original manufactured configuration due to the retractive influence of the film 136, if the film is elastomeric. Further details pertaining to the manufacture of neck-bonded laminates using a molten elastic film are provided in U.S. Pat. No. 5,514,470 to Haffner et al., which is incorporated by reference.

The film 136 may be made from any material which may be manufactured in sheet form. Generally, any suitable extendible or elastomeric film forming resins or blends containing the same may be utilized for the film 136.

Many elastomeric polymers are known to be suitable for forming extensible materials that are also elastic, i.e., materials that exhibit properties of stretch and recovery, such as elastic fibers and elastic fibrous web layers, and elastic film materials. Thermoplastic polymer compositions may desirably comprise any elastic polymer or polymers known to be suitable elastomeric fiber or film forming resins including, for example, elastic polyesters, elastic polyurethanes, elastic polyamides, elastic copolymers of ethylene and at least one vinyl monomer, block copolymers, and elastic polyolefins.

Examples of elastic block copolymers include those having the general formula A-B-A' or A-B, where A and A' are each a thermoplastic polymer endblock that contains a styrenic moiety such as a poly (vinyl arene) and where B is an elastomeric polymer midblock such as a conjugated diene or a lower alkene polymer such as for example polystyrene-poly (ethylene-butylene)-polystyrene block copolymers. Also included are polymers composed of an A-B-A-B tetrablock copolymer, as discussed in U.S. Pat. No. 5,332,613 to Taylor et al. An example of such a tetrablock copolymer is a styrene-poly(ethylene-propylene)-styrene-poly(ethylene-propylene) or SEPSEP block copolymer. These A-B-A' and A-B-A-B copolymers are available in several different formulations from Kraton Polymers U.S., L.L.C. of Houston, Tex. under the trade designation KRATON®. Other commercially available block copolymers include the SEPS or styrene-poly(ethylene-propylene)-styrene elastic copolymer available from Kuraray Company, Ltd., of Okayama, Japan, under the trade name SEPTON®.

Examples of elastic polyolefins include ultra-low density elastic polypropylenes and polyethylenes, such as those produced by "single-site" or "metallocene" catalysis methods. Such polymers are commercially available from the Dow Chemical Company of Midland, Mich. under the trade name ENGAGE®, and described in U.S. Pat. Nos. 5,278,272 and 5,272,236 to Lai et al. entitled "Elastic Substantially Linear Olefin Polymers". Also useful are certain elastomeric polypropylenes such as are described, for example, in U.S. Pat. No. 5,539,056 to Yang et al. and U.S. Pat. No. 5,596,052 to Resconi et al., incorporated herein by reference in their entireties, and polyethylenes such as AFFINITY® EG8200 from Dow Chemical of Midland, Mich. as well as EXACT® 4049, 4011 and 4041 from the ExxonMobil Chemical Company of Houston, Tex., as well as blends. Still other elastomeric polymers are available, such as the elastic polyolefin resins available under the trade name VISTAMAXX from the ExxonMobil Chemical Company, Houston, Tex., and the polyolefin (propylene-ethylene copolymer) elastic resins available under the trade name VERSIFY from Dow Chemical, Midlands, Michigan.

The film 136 may also be a pressure sensitive elastomer adhesive sheet. For example, the elastic material itself may be tacky or, alternatively, a compatible tackifying resin may be added to the extrudable elastomeric compositions described above to provide an elastomeric sheet that can act as a pressure sensitive adhesive, e.g., to bond the elastomeric sheet to a tensioned, necked nonelastic web. In regard to the tackifying resins and tackified extrudable elastomeric compositions, note the resins and compositions as described in J. S. Keiffer and T. J. Wisneski U.S. Pat. No. 4,789,699, filed 15 Oct. 1986 for "Ambient Temperature Bondable Elastomeric Nonwoven Web", the disclosure of which is hereby incorporated by reference.

The film 136 may also be a multilayer material in that it may include two or more individual coherent film layers. If the film is elastic, it may be stretched in the machine direction before being bonded to the necked nonwoven webs 122 and 222, to form a laminate which is elastic in both the machine direction and the cross direction. A similar laminate is disclosed in U.S. Pat. No. 5,116,662, which is incorporated by reference.

The necked nonwoven webs and laminates of the invention have improved basis weight uniformity due to the uniformity of the necking across the nonwoven web width. When the necked nonwoven webs are stretched to at least about 1.2 times, desirably about 1.25 times their initial machine direction length to cause neck stretching, each necked nonwoven web should have an average basis weight in its central region (defined as the central 70% of the width of the web) which is within about +7% of the average basis weight of the two edge regions (defined as the outer 15% of the width on each side of the web). Suitably, the average basis weight of the central region should be within about +5% of the average basis weight of the two edge regions. Desirably, the average basis weight of the central region should be within about +3% of the average basis weight of the two edge regions.

Various experiments have demonstrated that if a nonwoven web is corrugated prior to necking, to a corrugated width B about equal to the desired necked width C, then the necking will be more uniform across the width of the nonwoven web. In one instance, a corrugated polypropylene spunbond web necked 60.3% in the center and 61.9% at the edges. Without the corrugating step, the same spunbond web necked 47.5% in the center and 59.1% at the edges.

Also, a corrugated nonwoven web can be neck stretched to a higher level. In one instance, a corrugated polypropylene spunbond web broke at a necked width of 48.7 inches and a web from the same base roll (without corrugation) broke at a necked width of 61.5 inches. Both webs were subjected to increasing machine direction tension until breakage occurred.

While the embodiments of the invention disclosed herein are presently preferred, various modifications and improvements can be made without departing from the invention. The scope of the invention is indicated in the appended claims, and all changes that fall within the meaning and range of equivalents are intended to be embraced therein.

We claim:

1. A process for making a necked nonwoven material, comprising the steps of:
providing a nonwoven web having a first width A;
corrugating the nonwoven web in a cross direction using a plurality of laterally spaced castor rollers to provide a corrugated nonwoven web having a second width B less than the first width A;
passing the corrugated nonwoven web in a machine direction through a necking station wherein the corrugated nonwoven web is necked causing machine direction extension of the nonwoven web and at least some reduction of corrugations do to consolidation of the nonwoven web in the cross direction;
to thereby provide a necked nonwoven web having a third width C which is less than the first width A.

2. The process of claim 1, wherein the second width B is at least 25% less than the first width A.

3. The process of claim 1, wherein the second width B is at least 50% less than the first width A.

4. The process of claim 1, wherein the second width B is at least 75% less than the first width A.

5. The process of claim 1, wherein the second width B is closer to the third width C than to the first width A.

6. The process of claim 5, wherein the second width B is within about 15% of the third width C.

7. The process of claim 5, wherein the second width B is about the same as the third width C.

8. The process of claim 1, wherein the castor rollers are substantially uniformly spaced apart.

9. The process of claim 1, comprising at least four of the castor rollers.

10. The process of claim 1, comprising at least ten of the castor rollers.

11. The process of claim 1, comprising the steps passing the nonwoven web over one or more bowed rolls or bars and then directing the nonwoven web to the plurality of castor rollers.

12. The process of claim 1, wherein the castor rollers are swivel-mounted.

13. The process of claim 11, wherein at least one bowed roll or bar has a bow amount of at least about 10%.

14. The process of claim 1, wherein the necking station includes a first nip having a first surface velocity and a second nip having a second surface velocity 1.1-1.7 times the first surface velocity.

15. The process of claim 14, wherein the second surface velocity is about 1.2-1.5 times the first surface velocity.

16. The process of claim 1, wherein the necking station includes a plurality of S-wrap rolls having progressively higher surface velocities.

17. The process of claim 1, further comprising the step of laminating the necked nonwoven web to another layer.

18. The process of claim 17, wherein the other layer comprises an elastomeric film or an extendible film.

19. The process of claim 17, further comprising the step of laminating a second necked nonwoven web to the other layer.

20. The process of claim 1, wherein the necked nonwoven web is at least about 1.2 times the length of its initial machine direction length.

* * * * *